(12) United States Patent
Tatsuta et al.

(10) Patent No.: US 6,855,824 B2
(45) Date of Patent: Feb. 15, 2005

(54) PROCESSES FOR PREPARING QUINOLINE DERIVATIVES AND INTERMEDIATES THEREOF

(75) Inventors: Kuniaki Tatsuta, Tokyo (JP); Shigeki Kikuyama, Niigata (JP); Yoshin Tamai, Niigata (JP)

(73) Assignees: Kuraray Co., Ltd., Kurashiki (JP); Nissan Chemical Industries, Ltd., Tokyo (JP)

(*) Notice: Subject to any disclaimer, the term of this patent is extended or adjusted under 35 U.S.C. 154(b) by 168 days.

(21) Appl. No.: 10/204,312

(22) PCT Filed: Feb. 19, 2001

(86) PCT No.: PCT/JP01/01184
§ 371 (c)(1),
(2), (4) Date: Nov. 21, 2002

(87) PCT Pub. No.: WO01/60800
PCT Pub. Date: Aug. 23, 2001

(65) Prior Publication Data
US 2003/0125355 A1 Jul. 3, 2003

(30) Foreign Application Priority Data
Feb. 21, 2000 (JP) .......................................... 2000-042594
Feb. 21, 2000 (JP) .......................................... 2000-042595

(51) Int. Cl.[7] .............................................. C07D 215/12

(52) U.S. Cl. ........................ 546/174; 546/157; 546/173; 546/178; 546/179; 546/180

(58) Field of Search ................................ 546/157, 173, 546/174, 178, 179, 180

(56) References Cited

U.S. PATENT DOCUMENTS 5,856,336 A  1/1999  Fujikawa et al.

FOREIGN PATENT DOCUMENTS

| EP | 0 304 063 | 2/1989 |
|---|---|---|
| EP | 0 535 548 | 4/1993 |
| EP | 1 099 694 | 5/2001 |
| JP | 1-279866 | 11/1989 |
| JP | 8-27114 | 1/1996 |
| WO | WO 00/05213 | 2/2000 |

OTHER PUBLICATIONS

"Diethyl 2–(cyclohexylamino)vinylphosphonate" Organic Syntheses, vol. 53, pp. 44–48 1973.

Edward A. Fehnel: "Friedlaender syntheses with o–aminoaryl ketones. I. Acid–catalyzed condensations of o–aminobenzophenone with ketones" J. Org. Chem., vol. 31, pp. 2899–2902 1966.

Mikio Suzuki et al.: "Practical synthesis of quinoline nucleus of NK–104" HETEROCYLES, vol. 50, No. 1, pp. 479–483 1999.

Charles W. Spangler et al.: "Preparation of conjugated aromatic polyenals by Witting oxopropenylation" Synth Commun., vol. 18, No. 1, pp. 51–59 1988.

Koji Yamamoto et al.: "A Synthesis of a doubly–bridged [24] annulene" Tetrahedron Lett., vol. 27, No. 8, pp. 975–976 1986.

Gottfried Markl et al.: "Synthesis of diepoxy [16] annulene (6.2) by intramolecular McMurry coupling" Tetrahedron, vol. 55, No. 47, pp. 13407–13416 1999.

(List continued on next page.)

*Primary Examiner*—Patricia L. Morris
(74) *Attorney, Agent, or Firm*—Oblon, Spivak, McClelland, Maier & Neustadt, P.C.

(57) ABSTRACT

The present invention provides a production method of quinoline derivative (V)

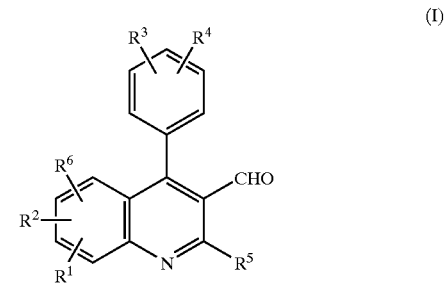

(I)

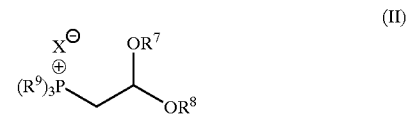

(II)

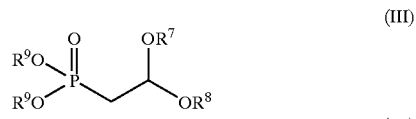

(III)

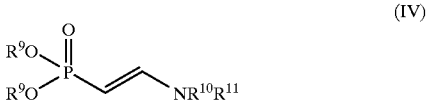

(IV)

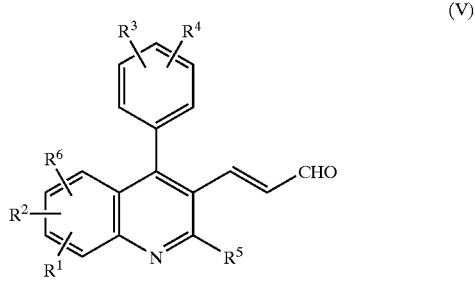

(V)

wherein each symbol is as defined in the Specification, which includes reacting quinolinecarbaldehyde (I) with any of the compounds (II) to (IV) in the presence of a base, followed by hydrolysis.

3 Claims, No Drawings

OTHER PUBLICATIONS

Jin Soon Cha et al.: "Exceptionally facile reduction of carboxylic esters to aldehydes by lithium aluminum hydride in the presence of diethylamine" J. Org. Chem., vol. 52, No. 24, pp. 5486–5487 1987.

M. Suzuki, et al., Bioorganic & Medicinal Chemistry Letters, vol. 9, No. 20, pp. 2977–2982, XP-004180521, "First Systematic Chiral Syntheses of Two Pairs of Enantiomers with 3,5–Dihydroxyheptenoic Acid Chain, Associated with a Potent Synthetic Statin NK–104", Oct. 18, 1999.

PROCESSES FOR PREPARING QUINOLINE DERIVATIVES AND INTERMEDIATES THEREOF

TECHNICAL FIELD

The present invention relates to a production method of a quinoline derivative and an intermediate thereof. The quinoline derivative obtained by the present invention is useful as a synthetic intermediate for pharmaceutical agents, agricultural chemicals and the like. For example, (E)-3-(4'-(4"-fluorophenyl)-2'-cyclopropylquinolin-3'-yl)propene aldehyde is an important synthetic intermediate for a quinoline mevalonolactone derivative known as an inhibitor of an HMG-CoA reducing enzyme which is a rate-determining enzyme for the biosynthesis of cholesterol.

BACKGROUND ART

As a synthetic method of a quinoline derivative, for example, (E)-3-(4'-(4"-fluorophenyl)-2'-cyclopropylquinolin-3'-yl)propene aldehyde, there are known (1) a method comprising reacting cis-1-ethoxy-2-(tri-n-butylstannyl)ethylene with butyllithium in tetrahydrofuran, reacting the resulting compound with 4-(4'-fluorophenyl)-2-cyclopropylquinoline-3-carbaldehyde at −60 to −78° C., and hydrolyzing the obtained vinyl ether compound in the presence of an acid catalyst; and (2) a method comprising reacting 4-(4'-fluorophenyl)-2-cyclopropylquinoline-3-carbaldehyde with alkoxycarbonylmethyl phosphonate to give the corresponding α,β-unsaturated carboxylic acid ester, reducing an ester moiety of this compound with, for example, a metal hydride such as diisobutyl aluminum hydride and the like to give an alcohol, and oxidizing the alcohol with an oxidant such as activated manganese dioxide and the like (see JP-A-1-279866, EP-A-304063, U.S. Pat. No. 5,856,336).

As regards the above-mentioned method (1), the organotin compound to be used is industrially difficult to obtain, and needs to be reacted at an extremely low temperature of −60 to −78° C., thus requiring special reaction equipment. As regards the above-mentioned method (2), the metal hydride to be used for reducing the ester moiety is difficult to handle. In addition, plural steps are necessary until the objective product is obtained by either method, which makes these methods not entirely advantageous as an industrial production method of a quinoline derivative such as (E)-3-(4'-(4"-fluorophenyl)-2'-cyclopropylquinolin-3'-yl)propene aldehyde.

As a synthetic method of quinolinecarbaldehyde, such as 4-(4'-fluorophenyl)-2-cyclopropylquinoline-3-carbaldehyde, which is an intermediate for the above-mentioned quinoline derivative, there are known (3) a method comprising reducing the corresponding quinoline carboxylic acid ester with various metal hydrides, such as diisobutylaluminum hydride and the like, to give the corresponding quinoline carbinol (4-(4'-fluorophenyl)-2-cyclopropyl-3-hydroxymethylquinoline), then oxidizing this compound with pyridinium chlorochromate, oxalyl chloride/dimethyl sulfoxide/tertiary amine (Swern oxidation), or sulfur trioxide pyridine complex and the like (see JP-A-1-279866, EP-A-304063, U.S. Pat. No. 5,856,336); and (4) a method comprising oxidizing 4-(4'-fluorophenyl)-2-cyclopropyl-3-hydroxymethylquinoline with a hypohalous acid salt in the presence of a nitroxy radical derivative (see JP-A-8-27114).

The above-mentioned (3) and (4) comprise oxidation of an alcohol moiety into aldehyde using the corresponding quinoline carbinol as a starting material for the production of quinolinecarbaldehyde, which requires complicated steps because quinoline carbinol needs to be obtained by reducing the corresponding quinoline carboxylic acid ester. In addition, pyridinium chlorochromate used as an oxidant in method (3) is associated with a problem of treatment of a waste liquid containing an environmentally harmful chromium ion, and byproduction of dimethyl sulfide that generates extreme odor under Swern oxidation conditions and conditions using a sulfur trioxide pyridine complex. For the oxidation reaction using a hypohalous acid salt, moreover, an environmentally harmful halogenated hydrocarbon, such as dichloromethane and the like, needs to be generally used as a solvent. Therefore, the above-mentioned methods are hardly considered an industrial production method of quinolinecarbaldehyde.

It is therefore an object of the present invention to provide a method capable of producing a quinoline derivative and an intermediate thereof efficiently and industrially advantageously by shorter steps, using chemicals that are industrially easily obtainable and easily handled.

DISCLOSURE OF THE INVENTION

According to the present invention, a production method of a quinoline derivative of the formula (V)

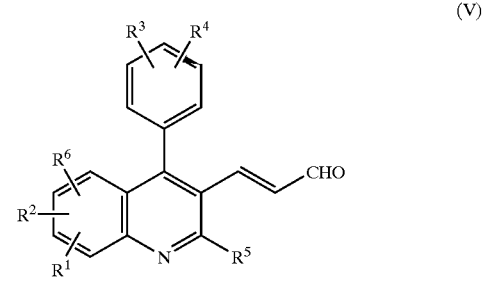

(V)

wherein $R^1$, $R^2$, $R^3$, $R^4$, $R^5$ and $R^6$ each independently represent a hydrogen atom, a halogen atom, a trifluoromethyl group, a trifluoromethoxy group, an optionally protected hydroxyl group, an alkyl group optionally having substituents, a cycloalkyl group optionally having substituents, an aryl group optionally having substituents, an aralkyl group optionally having substituents, an alkoxyl group optionally having substituents or an aryloxy group optionally having substituents (hereinafter to be abbreviated as quinoline derivative (V)), which comprises:

reacting a quinolinecarbaldehyde of the formula (I)

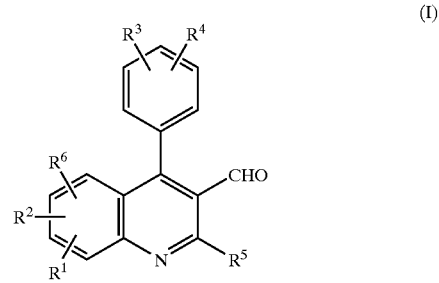

(I)

wherein $R^1$, $R^2$, $R^3$, $R^4$, $R^5$ and $R^6$ are as defined above (hereinafter to be abbreviated as quinolinecarbaldehyde (I)), with any of the following compounds (a) to (c) in the presence of a base, (a) a phosphonium salt compound of the formula (II)

(II)

wherein $R^7$ and $R^8$ each independently represent a hydrogen atom, an alkyl group optionally having substituents, an acyl group optionally having substituents or an aralkyl group optionally having substituents, or in combination represent an alkylene group, an arylene group or an aralkylene group, $R^9$ represents an alkyl group optionally having substituents or an aryl group optionally having substituents, and X represents a halogen atom (hereinafter to be abbreviated as phosphonium salt (II)), (b) a phosphonate compound of the formula (III)

(III)

wherein $R^7$, $R^8$ and $R^9$ are as defined above (hereinafter to be abbreviated as phosphonate (III)), and (c) a phosphonate compound of the formula (IV)

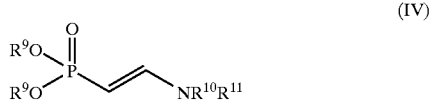

(IV)

wherein each $R^9$ is as defined above, and $R^{10}$ and $R^{11}$ each independently represent a hydrogen atom, an alkyl group optionally having substituents, a cycloalkyl group optionally having substituents, an aryl group optionally having substituents or an aralkyl group optionally having substituents, or in combination represent an alkylene group, an arylene group or an aralkylene group (hereinafter to be abbreviated as phosphonate (IV)), and then hydrolyzing the resulting compound, is provided.

In a preferable embodiment, $R^1$, $R^2$, $R^3$ and $R^6$ are hydrogen atoms, $R^4$ is a halogen atom, $R^5$ is an alkyl group having 1 to 6 carbon atoms or a cycloalkyl group having 3 to 6 carbon atoms, $R^7$ and $R^8$ are each independently an alkyl group having 1 to 6 carbon atoms, a cycloalkyl group having 3 to 6 carbon atoms, a phenyl group, a naphthyl group or a benzyl group, or in combination show an alkylene group having 2 to 6 carbon atoms or an arylene group having 6 to 10 carbon atoms, $R^9$ is an alkyl group having 1 to 6 carbon atoms or a phenyl group, and $R^{10}$ and $R^{11}$ are each independently an alkyl group having 1 to 6 carbon atoms, a cycloalkyl group having 3 to 6 carbon atoms, a phenyl group, a naphthyl group or a benzyl group, or in combination show an alkylene group having 2 to 6 carbon atoms or an arylene group having 6 to 10 carbon atoms.

In a more preferable embodiment, $R^4$ is a fluorine atom, $R^7$ and $R^8$ are each independently an alkyl group having 1 to 6 carbon atoms, or in combination show an alkylene group having 2 to 6 carbon atoms, and $R^{10}$ and $R^{11}$ are each independently an alkyl group having 1 to 6 carbon atoms, or in combination show an alkylene group having 2 to 6 carbon atoms.

According to the present invention, a production method of a quinolinecarbaldehyde of the formula (I)

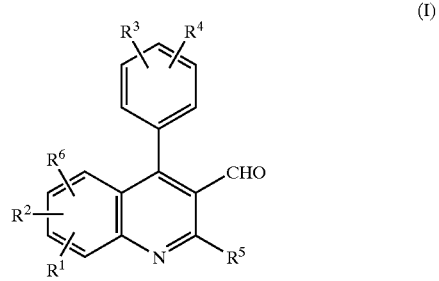

(I)

wherein $R^1$, $R^2$, $R^3$, $R^4$, $R^5$ and $R^6$ are as defined above, which comprises:

reducing a quinoline carboxylic acid ester of the formula (VI)

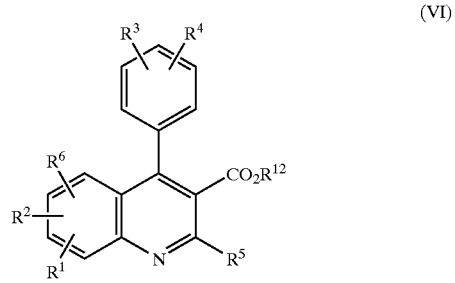

(VI)

wherein $R^1$, $R^2$, $R^3$, $R^4$, $R^5$ and $R^6$ are as defined above, and $R^{12}$ represents an alkyl group optionally having substituents, a cycloalkyl group optionally having substituents, an aryl group optionally having substituents or an aralkyl group optionally having substituents (hereinafter to be abbreviated as quinoline carboxylic acid ester (VI)), with an aluminum hydride complex compound in the presence of a secondary amine, is provided.

In a preferable embodiment, $R^1$, $R^2$, $R^3$ and $R^6$ are hydrogen atoms, $R^4$ is a halogen atom, $R^5$ is an alkyl group having 1 to 6 carbon atoms or a cycloalkyl group having 3 to 6 carbon atoms, and $R^{12}$ is an alkyl group having 1 to 6 carbon atoms, a cycloalkyl group having 3 to 6 carbon atoms, a phenyl group, a naphthyl group or a benzyl group.

In a more preferable embodiment, $R^4$ is a fluorine atom and $R^{12}$ is an alkyl group having 1 to 4 carbon atoms.

Each group in the above-mentioned formulas is defined as follows:

The alkyl group represented by $R^1$, $R^2$, $R^3$, $R^4$, $R^5$, $R^6$, $R^7$, $R^8$, $R^9$, $R^{10}$, $R^{11}$ and $R^{12}$ is exemplified by a straight or branched chain alkyl group preferably having 1 to 6, more preferably 1 to 4, carbon atoms. Examples thereof include methyl group, ethyl group, propyl group, isopropyl group, butyl group, isobutyl group, tert-butyl group and the like. These alkyl groups may have substituents and examples of the substituent include hydroxyl group; alkoxyl group preferably having 1 to 4 carbon atoms, such as methoxy group, ethoxy group, propoxy group, butoxy group and the like.

The cycloalkyl group represented by $R^1$, $R^2$, $R^3$, $R^4$, $R^5$, $R^6$, $R^{10}$, $R^{11}$ and $R^{12}$ is exemplified a cycloalkyl group preferably having 3 to 6 carbon atoms. Examples thereof include cyclopropyl group, cyclobutyl group, cyclopentyl group, cyclohexyl group and the like. These cycloalkyl groups may have substituents and examples of the substituent include hydroxyl group; alkyl group preferably having 1 to 6 carbon atoms, such as methyl group, ethyl group, propyl group, isopropyl group, butyl group, isobutyl group, tert-butyl group and the like; alkoxyl group preferably having 1 to 4 carbon atoms, such as methoxy group, ethoxy group, propoxy group, butoxy group and the like; aryl group preferably having 6 to 10 carbon atoms, such as phenyl group, p-methoxyphenyl group, p-chlorophenyl group and the like.

The aryl group represented by $R^1$, $R^2$, $R^3$, $R^4$, $R^5$, $R^6$, $R^9$, $R^{10}$, $R^{11}$ and $R^{12}$ is exemplified by an aryl group preferably having 6 to 10 carbon atoms. Examples thereof include phenyl group, naphthyl group and the like. These aryl groups may have substituents and examples of the substituent include hydroxyl group; alkyl group preferably having 1 to 6 carbon atoms, such as methyl group, ethyl group, propyl group, isopropyl group, butyl group, isobutyl group, tert-butyl group and the like; alkoxyl group preferably having 1 to 4 carbon atoms, such as methoxy group, ethoxy group, propoxy group, butoxy group and the like; aryl group preferably having 6 to 10 carbon atoms, such as phenyl group, p-methoxyphenyl group, p-chlorophenyl group and the like.

The aralkyl group represented by $R^1$, $R^2$, $R^3$, $R^4$, $R^5$, $R^6$, $R^7$, $R^8$, $R^{10}$, $R^{11}$ and $R^{12}$ is exemplified by an aralkyl group, which has alkyl group preferably having 1 to 6 carbon atoms as an alkyl moiety, and aryl group preferably having 6 to 10 carbon atoms as an aryl moiety. Examples thereof include benzyl group, naphthylmethyl group and the like. These aralkyl groups may have substituents and examples of the substituent include hydroxyl group; alkyl group preferably having 1 to 6 carbon atoms, such as methyl group, ethyl group, propyl group, isopropyl group, butyl group, isobutyl group, tert-butyl group and the like; alkoxyl group preferably having 1 to 4 carbon atoms, such as methoxy group, ethoxy group, propoxy group, butoxy group and the like; and aryl group preferably having 6 to 10 carbon atoms, such as phenyl group, p-methoxyphenyl group, p-chlorophenyl group and the like.

The halogen atom represented by $R^1$, $R^2$, $R^3$, $R^4$, $R^5$, $R^6$ and X is exemplified by fluorine atom, chlorine atom, bromine atom, iodine atom and the like, preferably fluorine atom.

The alkoxyl group represented by $R^1$, $R^2$, $R^3$, $R^4$, $R^5$ and $R^6$ is exemplified by a straight or branched chain alkoxyl group preferably having 1 to 4 carbon atoms. Examples thereof include methoxy group, ethoxy group, propoxy group, butoxy group and the like. These alkoxyl groups may have substituents and examples of the substituent include hydroxyl group; alkoxyl group preferably having 1 to 4 carbon atoms, such as methoxy group, ethoxy group, propoxy group, butoxy group and the like; aryl group preferably having 6 to 10 carbon atoms, such as phenyl group, p-methoxyphenyl group, p-chlorophenyl group and the like.

The aryloxy group represented by $R^1$, $R^2$, $R^3$, $R^4$, $R^5$ and $R^6$ is exemplified by aryloxy group, which has an aryl group preferably having 6 to 10 carbon atoms as an aryl moiety. Examples thereof include phenoxy group, tolyloxy group, naphthyloxy group and the like. These aryloxy groups may have substituents and examples of the substituent include hydroxyl group; alkyl group preferably having 1 to 6 carbon atoms, such as methyl group, ethyl group, propyl group, isopropyl group, butyl group, isobutyl group, tert-butyl group and the like; alkoxyl group preferably having 1 to 4 carbon atoms, such as methoxy group, ethoxy group, propoxy group, butoxy group and the like; and aryl group preferably having 6 to 10 carbon atoms, such as phenyl group, p-methoxyphenyl group, p-chlorophenyl group and the like.

The hydroxyl group represented by $R^1$, $R^2$, $R^3$, $R^4$, $R^5$ and $R^6$ may be protected. The protecting group for hydroxyl group is free of any particular limitation as long as it is generally used for protecting hydroxyl group, and is exemplified by aralkyl group such as benzyl group and the like; tri-substituted silyl group such as trimethylsilyl group, tert-butyldimethylsilyl group, tert-butyldiphenylsilyl group and the like; acetal-type protecting group such as methoxymethyl group, 1-ethoxyethyl group, tetrahydrofuranyl group, tetrahydropyranyl group and the like.

The acyl group represented by $R^7$ and $R^8$ is exemplified by alkylcarbonyl group wherein the alkyl moiety is a straight or branched chain alkyl group preferably having 1 to 6 carbon atoms, such as acetyl group and the like; arylcarbonyl group wherein the aryl moiety is an aryl group preferably having 6 to 10 carbon atoms, such as benzoyl group; and the like. These acyl groups may have substituents and examples of the substituent include hydroxyl group; alkyl group preferably having 1 to 6 carbon atoms such as methyl group, ethyl group, propyl group, isopropyl group, butyl group, isobutyl group, tert-butyl group and the like; alkoxyl group preferably having 1 to 4 carbon atoms such as methoxy group, ethoxy group, propoxy group, butoxy group and the like; and aryl group preferably having 6 to 10 carbon atoms, such as phenyl group, p-methoxyphenyl group, p-chlorophenyl group and the like.

The alkylene group represented by $R^7$ and $R^8$, or $R^{10}$ and $R^{11}$ in combination is exemplified by a straight or branched chain alkylene group preferably having 2 to 6 carbon atoms, such as ethylene group, propylene group, butylene group, pentylene group and the like. The arylene group represented by $R^7$ and $R^8$, or $R^{10}$ and $R^{11}$ in combination is exemplified by arylene group preferably having 6 to 10 carbon atoms, such as o-phenylene group, 2,3-naphthalenediyl group and the like. The aralkylene group represented by $R^7$ and $R^8$, or $R^{10}$ and $R^{11}$ in combination is exemplified by aralkylene group wherein the alkylene moiety is an alkylene group preferably having 2 to 6 carbon atoms, and wherein the arylene moiety is an arylene group preferably having 6 to 10 carbon atoms. Examples thereof include 1,2-benzo-2-butene group, 2,3-naphto-2-butene group and the like.

As a preferable quinolinecarbaldehyde (I) and quinoline derivative (V), a compound wherein $R^1$, $R^2$, $R^3$ and $R^6$ are hydrogen atoms, $R^4$ is a halogen atom, and $R^5$ is an alkyl group having 1 to 6 carbon atoms or a cycloalkyl group having 3 to 6 carbon atoms is mentioned.

As a more preferable quinolinecarbaldehyde (I) and quinoline derivative (V), a compound wherein $R^1$, $R^2$, $R^3$ and $R^6$ are hydrogen atoms, $R^4$ is a fluorine atom, and $R^5$ is an alkyl group having 1 to 6 carbon atoms or a cycloalkyl group having 3 to 6 carbon atoms is mentioned.

As a more preferable quinolinecarbaldehyde (I) and quinoline derivative (V), a compound wherein $R^1$, $R^2$, $R^3$ and $R^6$ are hydrogen atoms, $R^4$ is a fluorine atom, and $R^5$ is an isopropyl group or a cyclopropyl group is mentioned.

As a preferable phosphonium salt (II) and phosphonate (III), a compound wherein $R^7$ and $R^8$ are each independently an alkyl group having 1 to 6 carbon atoms, a cycloalkyl group having 3 to 6 carbon atoms, a phenyl group, a naphthyl group or a benzyl group, or in combination show an alkylene group having 2 to 6 carbon atoms or an arylene group having 6 to 10 carbon atoms, and $R^9$ is an alkyl group having 1 to 6 carbon atoms or a phenyl group is mentioned.

As a more preferable phosphonium salt (II) and phosphonate (III), a compound wherein $R^7$ and $R^8$ are each independently an alkyl group having 1 to 6 carbon atoms, or in combination show an alkylene group having 2 to 6 carbon atoms, $R^9$ is an alkyl group having 1 to 6 carbon atoms or a phenyl group is mentioned.

As a preferable phosphonate (IV), a compound wherein $R^9$ is an alkyl group having 1 to 6 carbon atoms or a phenyl group, and $R^{10}$ and $R^{11}$ are each independently an alkyl group having 1 to 6 carbon atoms, cycloalkyl group having 3 to 6 carbon atoms, phenyl group, naphthyl group or benzyl group, or in combination show an alkylene group having 2 to 6 carbon atoms or an arylene group having 6 to 10 carbon atoms is mentioned.

As a more preferable phosphonate (IV), a compound wherein $R^9$ is an alkyl group having 1 to 6 carbon atoms or a phenyl group, and $R^{10}$ and $R^{11}$ are each independently an alkyl group having 1 to 6 carbon atoms, or in combination show an alkylene group having 2 to 6 carbon atoms is mentioned.

As a preferable quinoline carboxylic acid ester (VI), a compound wherein $R^1$, $R^2$, $R^3$ and $R^6$ are hydrogen atoms, $R^4$ is a halogen atom, $R^5$ is an alkyl group having 1 to 6 carbon atoms or a cycloalkyl group having 3 to 6 carbon atoms, and $R^{12}$ is an alkyl group having 1 to 6 carbon atoms, cycloalkyl group having 3 to 6 carbon atoms, phenyl group, naphthyl group or benzyl group is mentioned.

As a more preferable quinoline carboxylic acid ester (VI), a compound wherein $R^1$, $R^2$, $R^3$ and $R^6$ are hydrogen atoms, $R^4$ is a fluorine atom, $R^5$ is an alkyl group having 1 to 6 carbon atoms or a cycloalkyl group having 3 to 6 carbon atoms, and $R^{12}$ is an alkyl group having 1 to 4 carbon atoms is mentioned.

As a more preferable quinoline carboxylic acid ester (VI), a compound wherein $R^1$, $R^2$, $R^3$ and $R^6$ are hydrogen atoms, $R^4$ is a fluorine atom, $R^5$ is an isopropyl group or a cyclopropyl group, and $R^{12}$ is an alkyl group having 1 to 4 carbon atoms is mentioned.

Production Method of Quinoline Derivative (V)

The production method of the quinoline derivative (V) of the present invention is characterized by reacting quinolinecarbaldehyde (I) with one of phosphonium salt (II), phosphonate (III) and phosphonate (IV) in the presence of a base and then subjecting the compound to hydrolysis. Namely, as shown in the following scheme 1, the method comprises a step for reacting an activated intermediate (phosphorane compound) produced by the reaction of a base with phosphonium salt (II), phosphonate (III) or phosphonate (IV), and quinolinecarbaldehyde (I) (Step 1), and a step of hydrolysis of an acetal group moiety or imino group moiety of the product (ia) or (ib) obtained by the above reaction (Step 2). In this production method, it is also possible to isolate an activated intermediate (phosphorane compound) produced by the reaction of a base with phosphonium salt (II), phosphonate (III) or phosphonate (IV), subjecting this intermediate to a reaction with quinolinecarbaldehyde (I), which method is also encompassed in the present invention.

[Scheme 1]

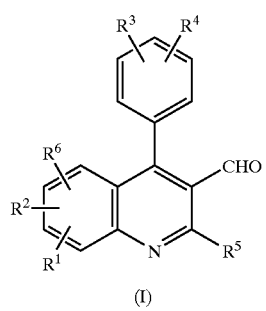

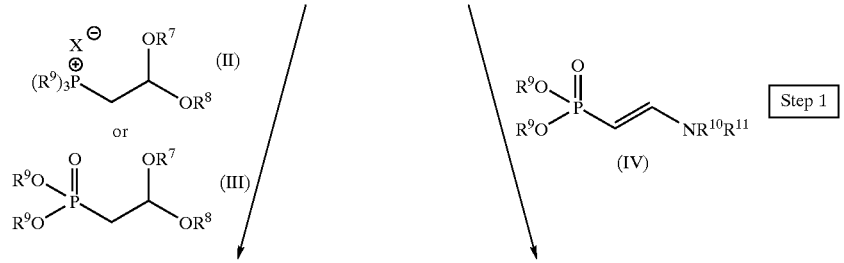

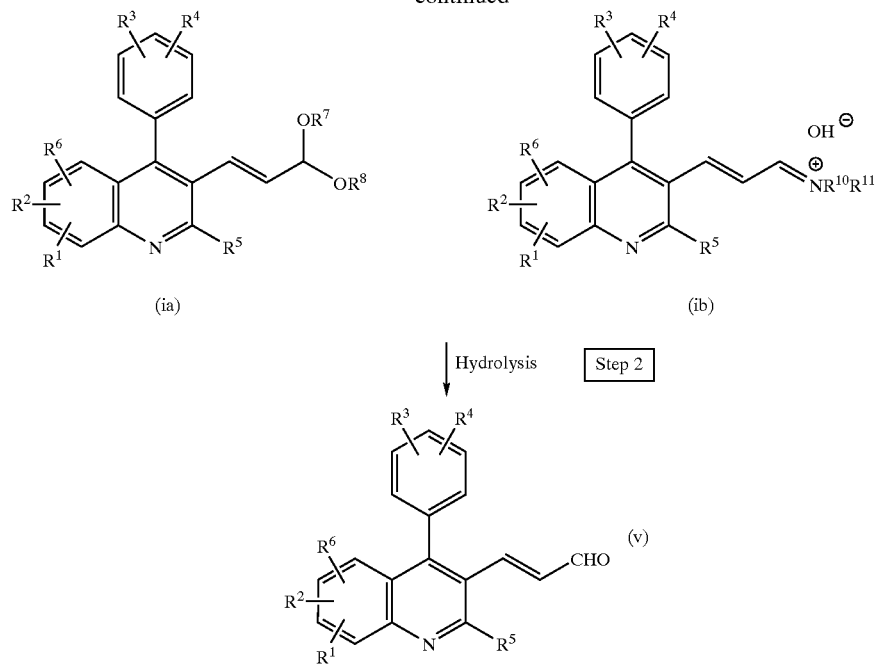

wherein each symbol is as defined above.

According to this method, quinoline derivative (V) can be produced advantageously by reacting quinolinecarbaldehyde (I) with phosphonium salt (II), phosphonate (III) or phosphonate (IV) in the presence of a base, thereby immediately reacting an activated intermediate (phosphorane compound) produced in the reaction system with quinolinecarbaldehyde (I), and subjecting the product obtained by this reaction to hydrolysis, with or without purification.

In the following, this method is explained by the steps.

[Step 1] Step for reaction of quinolinecarbaldehyde (I) with phosphonium salt (II), phosphonate (III) or phosphonate (IV) in the presence of a base Examples of the phosphonium salt (II) include (1,3-dioxolan-2-ylmethyl)triphenyl phosphonium bromide, (1,3-dioxolan-2-ylmethyl)triphenyl phosphonium iodide and the like. Examples of the phosphonate (III) include diethyl phosphonoacetaldehyde diethylacetal, dimethyl phosphonoacetaldehyde dimethylacetal and the like. Examples of the phosphonate (IV) include diethyl-2-(cyclohexylamino)-vinylphosphonate, dimethyl-2-(cyclohexylamino) vinylphosphonate and the like.

The amount of phosphonium salt (II), phosphonate (III) or phosphonate (IV) to be used is preferably within the range of 1 to 10-fold moles, more preferably within the range of 1 to 2-fold moles, relative to 1 mole of quinolinecarbaldehyde (I).

Examples of the base include alkali metal carbonates such as sodium carbonate, potassium carbonate and the like; alkali metal hydroxides such as sodium hydroxide, potassium hydroxide and the like; organolithium compounds such as methyllithium, ethyllithium, n-butyllithium, sec-butyllithium, tert-butyllithium, phenyllithium and the like; alkylmagnesium halides such as methylmagnesium chloride, ethylmagnesium bromide and the like; metal amides such as lithium amide, sodium amide, potassium amide, lithium diethylamide, lithium diisopropylamide, lithium bis(trimethylsilyl)amide, sodium bis(trimethylsilyl) amide, potassium bis(trimethylsilyl)amide, bromomagnesium diisopropylamide and the like; metal alkoxides such as lithium methoxide, sodium methoxide, sodium ethoxide, sodium tert-butoxide, potassium tert-butoxide and the like; alkali metal hydrides such as lithium hydride, sodium hydride, potassium hydride and the like. Of these, sodium hydride, n-butyllithium, tert-butyllithium and potassium tert-butoxide are preferably used from the aspects of the high stability of the activated intermediate (phosphorane compound) produced, and the like. The amount of the base to be used is free of any particular limitation, but it is generally preferably not less than 0.1 mole, more preferably within the range of 0.5 to 2-fold moles, relative to 1 mole of phosphonium salt (II), phosphonate (III) or phosphonate (IV), for a smooth progress of the reaction.

The step is preferably carried out in the presence of a solvent. The solvent to be used is free of any particular limitation as long as it does not adversely affect the reaction. Examples thereof include aliphatic hydrocarbons such as pentane, hexane, heptane, cyclohexane, methylcyclohexane and the like; aromatic hydrocarbons such as benzene, toluene, xylene and the like; alcohols such as methanol, ethanol, isopropanol, n-butanol, tert-butanol and the like; ethers such as diethyl ether, diisopropyl ether, tert-butyl methyl ether, tetrahydrofuran, dioxane and the like; halogenated hydrocarbons such as methylene chloride, chloroform, 1,2-dichloroethane and the like; nitriles such as acetonitrile, benzonitrile and the like; nitrogen-containing aromatic compounds such as pyridine and the like; amides such as dimethylformamide, N-methylpyrrolidone, N,N'-dimethylimidazolidinone, hexamethylphosphoric triamide and the like; dimethyl sulfoxide, N,N,N', N'-tetramethylethylenediamine, ammonia; and mixtures thereof. Of these, from the aspect of the stability of the activated intermediate (phosphorane compound) produced in the reaction system, aromatic hydrocarbons such as benzene, toluene, xylene and the like; ethers such as diethyl ether, diisopropyl ether, tert-butyl methyl ether, tetrahydrofuran, dioxane and the like; dimethylformamide and dimethyl sulfoxide are preferable. The amount of the solvent to be used is free of any particular limitation, but it is generally preferably 1 to 200-fold weight, more preferably 5 to 20-fold weight, relative to quinolinecarbaldehyde (I).

While the reaction temperature varies depending on the kind of phosphonium salt (II), phosphonate (III) or phosphonate (IV) to be used, the kind of a base to be used and the kind of a solvent to be used, it is generally preferably within the range of −100 to 100° C., more preferably within the range of −50 to 30° C. While the reaction time also varies depending on the reaction temperature, it is generally preferably within the range of 0.1 to 24 hours.

The reaction is preferably carried out by dissolving phosphonium salt (II), phosphonate (III) or phosphonate (IV) in a solvent under an inert gas atmosphere such as argon and the like, adding a base to this solution, adding quinolinecarbaldehyde (I), and stirring the mixture at a predetermined temperature. After the completion of the reaction, the reaction mixture is poured into water, extracted with organic solvent such as ethyl acetate, hexane and the like, and if necessary, the extract is washed with water, saturated aqueous sodium chloride solution, aqueous sodium hydrogen carbonate solution and the like, dried over a desiccant such as anhydrous sodium sulfate, anhydrous magnesium sulfate and the like, and concentrated to give a crude product. The obtained crude product can be isolated and purified as necessary by a general purification method such as recrystallization, distillation, column chromatography and the like, which may be followed by hydrolysis of an acetal group moiety or imino group moiety. Alternatively, the crude product may be subjected to a hydrolysis step without purification.

[Step 2] Step for hydrolysis of acetal group moiety or imino group moiety of the product obtained from Step 1

Typical hydrolysis reaction conditions for reacting an acid in a solvent containing water can be used. The amount of the water to be used is free of any particular limitation, and it is generally preferably within the range of not less than 1 mole, more preferably within the range of 1 to 10-fold moles, relative to 1 mole of quinolinecarbaldehyde (I), which is used as a starting material in the previous step.

Examples of the acid include mineral acids such as hydrochloric acid, sulfuric acid, phosphoric acid, perchloric acid and the like; organic acids such as acetic acid, propionic acid, p-toluenesulfonic acid, methanesulfonic acid, oxalic acid and the like, a hydrate thereof and a salt thereof. The amount of the acid to be used is free of any particular limitation, and it is generally preferably within the range of 0.01 to 5-fold moles, relative to the amount of quinolinecarbaldehyde (I), which is used as a starting material in the previous step.

The hydrolysis step is preferably carried out in the presence of a solvent. The solvent to be used is free of any particular limitation as long as it does not adversely affect the reaction. Examples thereof include alcohols such as methanol, ethanol, propanol, isopropanol, butanol, sec-butanol, tert-butanol and the like; ethers such as diethyl ether, tetrahydrofuran, dimethoxyethane and the like; hydrocarbons such as pentane, hexane, heptane, octane, petroleum ether, benzene, toluene, xylene and the like; amides such as dimethylformamide, N-methylpyrrolidone, N,N'-dimethylimidazolidinone, hexamethylphosphoric triamide and the like; nitrites such as acetonitrile and the like; dimethyl sulfoxide; and mixed solvents thereof. The amount of the solvent to be used is free of any particular limitation, and it is generally preferably within the range of 1 to 200-fold weight, relative to the amount of quinolinecarbaldehyde (I), which is used as a starting material in the previous step.

While the reaction temperature varies depending on the kind of an acid to be used and the kind of a solvent to be used, it is generally preferably within the range of 0 to 100° C. While the reaction time also varies depending on the reaction temperature, it is generally preferably within the range of 1 to 24 hours.

The quinoline derivative (V) obtained in this way can be isolated and purified by a method generally used for isolation and purification of organic compounds. For example, a base, such as aqueous sodium hydrogen carbonate solution, sodium methoxide and the like, is added as necessary to the reaction mixture after completion of the reaction, to neutralize the acid, and the mixture is extracted with an organic solvent such as diethyl ether, ethyl acetate, methylene chloride and the like. The extract is washed as necessary with water, saturated aqueous sodium chloride solution, aqueous sodium hydrogen carbonate solution and the like to remove acidic substance and water-soluble substance, dried over a desiccant such as anhydrous sodium sulfate, anhydrous magnesium sulfate and the like, and concentrated to give a crude product. The obtained crude product is purified by distillation, chromatography, recrystallization and the like.

The phosphonium salt (II) to be used for this method, such as (1,3-dioxolan-2-ylmethyl)triphenyl phosphonium bromide, can be easily synthesized by, for example, reacting bromoacetaldehyde ethylene acetal with triphenylphosphine. Phosphonate (III), such as diethyl phosphonoacetaldehyde diethyl acetal, can be synthesized by reacting bromoacetaldehyde diethyl acetal with triethyl phosphite. Phosphonate (IV), such as diethyl-2-(cyclohexylamino)-vinylphosphonate, can be synthesized by hydrolyzing the acetal moiety of diethyl phosphonoacetaldehyde diethyl acetal, and reacting the obtained aldehyde with cyclohexylamine (see Organic Syntheses, vol. 53, p. 44 (1973)).

[Production Method of Quinolinecarbaldehyde (I)]

The production method of quinolinecarbaldehyde (I) of the present invention is characterized by the reduction of quinoline carboxylic acid ester (VI) with an aluminum hydride complex compound in the presence of a secondary amine.

Examples of the aluminum hydride complex compound include sodium aluminum hydride, lithium aluminum hydride and sodium bis(2-methoxyethoxy)aluminum hydride. Of these, lithium aluminum hydride and sodium bis(2-methoxyethoxy)aluminum hydride are particularly preferably used in view of availability and handleability. The amount of the aluminum hydride complex compound to be used is preferably within the range of 0.5 to 10-fold moles, more preferably within the range of 1 to 5-fold moles for a smooth progress of the reaction, relative to the quinoline carboxylic acid ester (VI).

Examples of the secondary amine include chain aliphatic secondary amines such as dimethylamine, ethylmethylamine, diethylamine, methylisopropylamine, dipropylamine, diisopropylamine, methylbutylamine, ethylbutylamine, dibutylamine, diisobutylamine, dipentylamine, methylhexylamine, dihexylamine, dioctylamine, N-propylcyclopropylmethylamine, N-methylcyclohexylamine, N-ethylcyclohexylamine, N-isopropylcyclohexylamine, dicyclohexylamine, N-methylcyclodecylamine, dibenzylamine, N-ethylbenzylamine, N-isopropylbenzylamine, N-butylbenzylamine, N-benzylphenethylamine, bis(2-methoxyethyl)amine, methylaminoacetaldehyde dimethyl acetal, 2-methylaminomethyl-1,3-dioxolane and the like; cyclic aliphatic secondary amines such as 2-methylaziridine, azetidine, pyrrolidine, pyrroline, piperidine, pipecoline, dimethylpiperidine, 1-piperonylpiperidine, 4-benzylpiperidine, 4-phenylpiperidine, 4-piperidinopiperidine, hexamethylenimine, heptamethylenimine, 2-methyl-2-imidazoline, 2-phenyl-2-imidazoline, 1-methylpiperazine, 1-phenylpiperazine, 1-(2-pyridyl)piperazine, 1-(4-fluorophenyl)piperazine, 1-benzylpiperazine, 1-methoxyphenylpiperazine, 3-azabicyclo[3.2.2]nonane, morpholine, thiomorpholine, thiazolidine, indoline, 2-methylindoline, 2,3-dimethylindoline, perhydroindole, 1,2,3,4-tetrahydroquinoline, decahydroquinoline, 1,2,3,4-tetrahydroisoquinoline, iminodibenzyl, phenoxazine, phenothiazine, N,N,N'-trimethylethylenediamine, 3,3'-iminobis(N,N-dimethylpropylamine), N'-benzyl-N,N-dimethylethylenediamine and the like; and aromatic secondary amines such as N-methylaniline, N-ethylaniline, N-propylaniline, diphenylamine, phenylbenzylamine, N-butylbenzylamine, N-ethyltoluidine, 3-methoxydiphenylamine, N-phenyl-2-naphthylamine, 2-methylaminopyridine, 2-anilinopyridine, 2-benzylaminopyridine and the like. Of these, diethylamine, morpholine and 1-methylpiperazine are particularly preferably used for a smooth progress of the reaction.

While the amount of the secondary amine to be used varies depending on the kind of an aluminum hydride complex compound to be used, it is preferably a molar amount corresponding to the number of hydrogen atoms, which this aluminum hydride complex compound has, minus 0.5 to 1.5, particularly preferably minus 0.8 to 1.2, per 1 mole of the aluminum hydride complex compound. When a lithium aluminum hydride is used as an aluminum hydride complex compound, for example, because lithium aluminum hydride has four hydrogen atoms per 1 molecule, a secondary amine is preferably used in the range of 2.5 to 3.5-fold moles per 1 mole of lithium aluminum hydride. When sodium bis(2-methoxyethoxy)aluminum hydride is used as an aluminum hydride complex compound, because sodium bis(2-methoxyethoxy)aluminum hydride has two hydrogen atoms per molecule, a secondary amine is preferably used in the range of 0.5 to 1.5-fold moles, per 1 mole of sodium bis(2-methoxyethoxy)aluminum hydride.

The reaction is preferably carried out in the presence of a solvent. The solvent to be used is free of any particular limitation as long as it does not adversely affect the reaction. Examples thereof include aliphatic hydrocarbons such as pentane, hexane, heptane, octane, petroleum ether and the like; aromatic hydrocarbons such as benzene, toluene, xylene, cumene and the like; ethers such as diethyl ether, tetrahydrofuran, diisopropyl ether, dimethoxyethane, dibutyl ether and the like; mixed solvents thereof and the like. The amount of the solvent to be used is preferably within the range of 0.1 to 200-fold weights, more preferably within the range of 1 to 20-fold weights for a smooth progress of the reaction, relative to the quinoline carboxylic acid ester (VI).

The reaction temperature is preferably within the range of from −70° C. to the boiling point of the solvent to be used, more preferably within the range of −30° C. to 30° C. for a smooth progress of the reaction. In addition, while the reaction time varies depending on the reaction temperature, it is generally preferably within the range of 0.5 to 24 hours.

For the reaction, a method comprising adding dropwise a secondary amine to a solution obtained by mixing an aluminum hydride complex compound and a solvent, and adding this mixture to a solution obtained by dissolving quinoline carboxylic acid ester (VI) in a solvent and adjusting to a predetermined temperature, or a method comprising adding dropwise quinoline carboxylic acid ester (VI) or a solution obtained by dissolving quinoline carboxylic acid ester (VI) in a solvent to a mixture obtained by dropwise addition of a secondary amine to a solution obtained by mixing an aluminum hydride complex compound and a solvent, and reacting the mixture at a predetermined temperature, is preferable.

The quinolinecarbaldehyde (I) obtained in this way can be isolated and purified by a method generally used for isolation and purification of organic compounds. For example, an acidic aqueous solution such as hydrochloric acid, aqueous sulfuric acid solution, aqueous acetic acid solution and the like is added to a reaction mixture, or after addition of a reaction mixture to these acidic aqueous solutions, an organic layer is separated, dried over a desiccant such as anhydrous sodium sulfate, anhydrous magnesium sulfate and the like, and concentrated, and the obtained crude product is purified as necessary by distillation, recrystallization, sublimation, chromatography and the like. Alternatively, a saturated aqueous solution of an inorganic salt such as sodium sulfate, sodium chloride and the like, is added to a reaction mixture to allow precipitation of an aluminum salt, and after removing this salt by filtration, an organic layer is separated from the filtrate and a crude product can be obtained from the organic layer.

The quinoline carboxylic acid ester (VI), such as 4-(4'-fluorophenyl)-2-cyclopropylquinoline-3-carboxylic acid ester, which is a starting substance of this method, can be easily synthesized by condensing 2-amino-4'-fluorobenzophenone with 3-cyclopropyl-3-oxopropanoic acid ester in the presence of an acid catalyst [see Journal of Organic Chemistry (J. org. Chem.), vol. 31, p. 2899 (1966); Heterocycles, vol. 50, p. 479 (1999)].

The present invention is explained in detail in the following by referring to Examples, which are not to be construed as limitative.

EXAMPLE 1

Lithium aluminum hydride (0.569 g, 15 mmol) was placed in a 50 ml volume three-necked flask equipped with a thermometer, a magnetic stirrer and a dropping funnel, and tetrahydrofuran (10 ml) was added as a solvent, followed by replacement of the system with nitrogen. To this solution was added dropwise morpholine (4.18 g, 48 mmol) gradually at room temperature, and after completion of the addition, the mixture was stirred at room temperature for 1 hr. This solution was cooled to 0° C. and a solution obtained by dissolving methyl 4-(4'-fluorophenyl)-2-cyclopropylquinoline-3-carboxylate (3.21 g, 10 mmol) in tetrahydrofuran (9.63 g) was added dropwise to this solution while maintaining the inner temperature to not higher than 0° C. After the completion of the addition, the mixture was stirred for 2 more hours at 10 to 20° C. This reaction mixture was added dropwise to a 15% aqueous sulfuric acid solution (50 ml) while maintaining the inner temperature to not higher than 10° C., and then, toluene (50 ml) was added to the mixture. The organic layer was separated from the mixture and the aqueous layer was extracted with toluene (10 ml). The extract was combined with the organic layer obtained earlier and the mixture was washed with water (30 ml), dried over anhydrous sodium sulfate, then low boiling point components, such as the solvent and the like, were removed under reduced pressure. The obtained residue was purified by column chromatography (eluent: hexane-ethyl acetate mixture) to give 4-(4'-fluorophenyl)-2-cyclopropylquinoline-3-carbaldehyde (2.27 g, yield 77%) as a pale-yellow solid having the following properties.

$^1$H-NMR (300 MHz, CDCl$_3$, TMS, ppm) δ: 1.08–1.14 (2H, m), 1.37–1.40(2H, m), 3.20–3.26(1H, m), 7.24–7.48

(6H, m), 7.76(1H, ddd, J=1.8, 6.5, 8.4 Hz), 7.97–8.00(1H, m), 10.06(1H, s)

EXAMPLE 2

By the reaction and post-treatment in the same manner as in Example 1 except that butyl 4-(4'-fluorophenyl)-2-cyclopropylquinoline-3-carboxylate (3.63 g, 10 mmol) was used instead of methyl 4-(4'-fluorophenyl)-2-cyclopropylquinoline-3-carboxylate, 4-(4'-fluorophenyl)-2-cyclopropylquinoline-3-carbaldehyde (2.16 g, yield 74%) was obtained.

EXAMPLE 3

By the reaction and post-treatment in the same manner as in Example 1 except that diethylamine (3.51 g, 48 mmol) was used instead of morpholine, 4-(4'-fluorophenyl)-2-cyclopropylquinoline-3-carbaldehyde (2.01 g, yield 69%) was obtained.

EXAMPLE 4

70% Toluene solution (57.8 g, 200 mmol) of sodium bis(2-methoxyethoxy) aluminum hydride was placed in a 200 ml three-necked flask equipped with a thermometer, a magnetic stirrer and a dropping funnel, and toluene (100 ml) was added as a solvent, which was followed by replacement of the system with nitrogen. To this solution was added dropwise morpholine (13.9 g, 160 mmol) gradually at room temperature, and after completion of the dropwise addition, the mixture was stirred at room temperature for 1 hr.

Methyl 4-(4'-fluorophenyl)-2-cyclopropylquinoline-3-carboxylate (32.1 g, 100 mmol) and toluene (300 ml) were placed in a different 1000 ml three-necked flask, and the system was replaced by nitrogen and cooled to −5° C. To this solution was added dropwise the entire amount of a toluene solution prepared earlier by mixing sodium bis(2-methoxyethoxy)aluminum hydride and morpholine, while maintaining the inner temperature to not higher than 0° C., and after completion of the addition, the mixture was heated to room temperature and stirred for 3 hr. This reaction mixture was added dropwise to a 15% aqueous sulfuric acid solution (200 ml) while maintaining the inner temperature to not higher than 10° C. The organic layer was separated from the mixture and the aqueous layer was extracted with toluene (30 ml). The extract was combined with the organic layer obtained earlier. The mixture was washed with water (100 ml), dried over anhydrous sodium sulfate and concentrated. The obtained residue was recrystallized from diisopropyl ether to give 4-(4'-fluorophenyl)-2-cyclopropylquinoline-3-carbaldehyde (22.4 g, yield 76%).

EXAMPLE 5

Under an argon atmosphere, anhydrous dimethyl sulfoxide (10.0 ml) was added to (1,3-dioxolan-2-ylmethyl) triphenyl phosphonium bromide (1.55 g, 3.61 mmol) and dissolved therein. To this solution was added dropwise tert-butyllithium (1.51 M, n-pentane solution, 2.40 ml, 3.62 mmol) at 20 to 30° C. over 2 min. The mixture was stirred at room temperature for 15 min and a solution obtained by dissolving 4-(4'-fluorophenyl)-2-cyclopropylquinoline-3-carbaldehyde (1.00 g, 3.44 mmol) in anhydrous dimethyl sulfoxide (5 ml) was added dropwise to this solution at 20 to 30° C. over 5 min. After completion of the addition, the mixture was stirred at the same temperature for 90 min. Water (10 ml) was added to the reaction mixture and the organic layer was separated. The aqueous layer was extracted twice with hexane (20 ml) and the extracts were combined with the organic layer separated earlier. The mixture was washed twice with water (10 ml), dried over anhydrous sodium sulfate and concentrated under reduced pressure. Tetrahydrofuran (20 ml) was added to the obtained crude product to allow dissolution, and 2 mol/l hydrochloric acid (10 ml) was added. The mixture was stood at room temperature for 30 min. Tetrahydrofuran was evaporated under reduced pressure from this mixture and the obtained red residue was dissolved in chloroform (10 ml). Hexane (30 ml) and saturated aqueous sodium hydrogen carbonate solution (50 ml) were added to the solution, and the organic layer was separated. The aqueous layer was extracted twice with hexane (50 ml) and the extracts were combined with the organic layer separated earlier and concentrated. The obtained crude product was purified by column chromatography to give (E)-3-(4'-(4"-fluorophenyl)-2'-cyclopropylquinolin-3'-yl)propene aldehyde (0.99 g, yield 90.9%) as pale-yellow crystals having the following properties. melting point: :124–132° C.

$^1$H-NMR (600 MHz, CDCl$_3$, TMS, ppm) δ:1.08–1.13 (2H, m, CH$_2$), 1.41–1.45(2H, m, CH$_2$), 2.32–2.38(1H, m, CH), 6.45(1H, dd, J=8, 16 Hz), 7.22–7.25(4H, m, Ar-H), 7.35–7.39(2H, m, Ar-H), 7.56(1H, d, J=16 Hz), 7.67(1H, ddd, J=3, 6, 8 Hz, Ar-H), 7.98(1H, d, J=8 Hz, Ar-H), 9.51(1H, d, J=8 Hz).

EXAMPLE 6

Under an argon atmosphere, 60% oily sodium hydride (165 mg, 4.12 mmol) was heated to 60° C. with stirring in tetrahydrofuran (825 mg). To this solution was added dropwise a solution obtained by dissolving anhydrous dimethyl sulfoxide (386 mg, 4.94 mmol) in tetrahydrofuran (825 mg). After stirring for 2 hr, the mixture was cooled to 20° C. Then, a mixture of sodium hydride, anhydrous dimethyl sulfoxide and tetrahydrofuran prepared earlier was added to (1,3-dioxolan-2-ylmethyl) triphenyl phosphonium bromide (2.21 g, 5.15 mmol) in tetrahydrofuran (8.84 g) under argon atmosphere with stirring. The mixture was stirred for 1 hr and cooled to 0° C. To this solution was added dropwise a solution obtained by dissolving 4-(4'-fluorophenyl)-2-cyclopropylquinoline-3-carbaldehyde (1.00 g, 3.44 mmol) in tetrahydrofuran (4 g) at 0 to 5° C. over 5 min, and after completion of the addition, the mixture was stirred at the same temperature for 60 min. Water (5 g) was added to the reaction mixture and the solvent was evaporated under reduced pressure. The precipitated solid was dissolved in toluene (10 g) and washed twice with water (10 g). 0.5 mol/l Hydrochloric acid (10 ml) was added and the mixture was stirred for 5 hr and left standing. The lower layer was separated and the organic layer was washed successively with saturated aqueous sodium hydrogen carbonate solution (10 g) and water (10 g). The solvent was evaporated and the obtained crude product was purified by column chromatography to give (E)-3-(4'-(4"-fluorophenyl)-2'-cyclopropylquinolin-3'-yl)propene aldehyde (0.93 g, yield 85.4%).

EXAMPLE 7

Tetrahydrofuran (10 ml) was added to diethyl phosphonoacetaldehyde diethyl acetal (1.05 g, 4.12 mmol) under an argon atmosphere to allow dissolution and the solution was cooled to −30 to −20° C. To this solution was added dropwise n-butyllithium (1.6 M, n-hexane solution, 2.60 ml, 4.16 mmol) at −30 to −20° C. over 5 min. The mixture was stirred at the same temperature for 1 hr and a solution obtained by dissolving 4-(4'-fluorophenyl)-2-cyclopropylquinoline-3-carbaldehyde (1.00 g, 3.44 mmol) in tetrahydrofuran (10 ml) was added dropwise at −30 to −20° C. over 5 min. After the completion of the addition, the mixture was heated to room temperature and stirred for 2 hr. The reaction mixture was added to ice water (100 ml) and extracted 3 times with ethyl acetate (50 ml). The extracts were combined, washed with saturated brine, dried over anhydrous sodium sulfate and concentrated. Toluene (20 ml) and 10% aqueous perchloric acid solution (10 ml) were added to the obtained residue and the mixture was heated to 40 to 50° C. for 1 hr. The mixture was cooled to room temperature, neutralized with aqueous sodium hydrogen carbonate solution and extracted 3 times with toluene (50 ml). The extracts were combined, washed with saturated brine, dried over anhydrous sodium sulfate and concentrated. The obtained crude product (1.6 g) was purified by column chromatography to give (E)-3-(4'-(4"-fluorophenyl)-2'-cyclopropylquinolin-3'-yl)propene aldehyde (0.92 g, yield 84.5%).

EXAMPLE 8

Sodium hydride (98.3 mg, 4.10 mmol) was suspended in tetrahydrofuran (10 ml) under an argon atmosphere, and the obtained solution was cooled to −10 to −5° C. To this solution was added dropwise a solution obtained by dissolving diethyl-2-(cyclohexylamino)vinylphosphonate (1.34 g, 5.13 mmol) in tetrahydrofuran (10 ml) over 5 min, and after completion of the addition, the mixture was stirred at −10 to −5° C. for 1 hr. To this solution was added dropwise a solution obtained by dissolving 4-(4'-fluorophenyl)-2-cyclopropylquinoline-3-carbaldehyde (1.00 g, 3.44 mmol) in tetrahydrofuran (20 ml) at −10 to −5° C. over 5 min, and after completion of the addition, the mixture was heated to refluxing temperature and stirred for 1 hr. The reaction mixture was cooled to room temperature and added to ice water (300 ml). The mixture was extracted 3 times with ethyl acetate (100 ml) and the extracts were combined, washed with saturated brine, dried over anhydrous sodium sulfate and concentrated. To the obtained residue was added a solution obtained by dissolving toluene (20 ml) and oxalic acid dihydrate (1.5 g, 11.9 mmol) in water (20 ml) and the mixture was heated to 60 to 70° C. for 1 hr. The mixture was cooled to room temperature and the organic layer and the aqueous layer were separated. The aqueous layer was extracted twice with toluene (20 ml). The extracts were combined with the organic layer separated earlier, washed with saturated brine, dried over anhydrous sodium sulfate and concentrated. The obtained crude product (1.6 g) was purified by column chromatography to give (E)-3-(4'-(4"-fluorophenyl)-2'-cyclopropylquinolin-3'-yl) propene aldehyde (0.95 g, yield 86.5%).

INDUSTRIAL APPLICABILITY

According to the present invention, a quinoline derivative useful as a synthetic intermediate for pharmaceutical agents, agricultural chemicals and the like, such as a quinoline derivative (e.g., (E)-3-(4'-(4"-fluorophenyl)-2'-cyclopropylquinolin-3'-yl)propene aldehyde), which is an important synthetic intermediate for a quinoline mevalonolactone derivative known as an inhibitor of an HMG-COA reducing enzyme which is a rate-determining enzyme for the biosynthesis of cholesterol, and an intermediate thereof, can be produced efficiently and industrially advantageously by shorter steps.

This application is based on patent application Nos. 2000-042594 and 2000-042595 filed in Japan, the contents of which are hereby incorporated by reference.

What is claimed is:

1. A production method of a quinoline derivative of the formula (V)

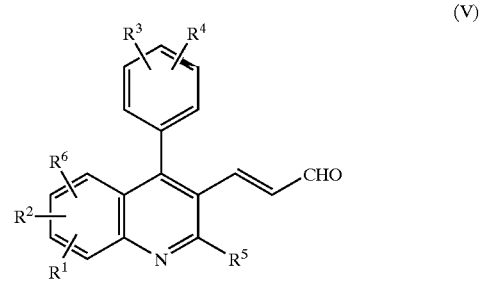

(V)

wherein $R^1$, $R^2$, $R^3$, $R^4$, $R^5$ and $R^6$ each independently represent a hydrogen atom, a halogen atom, a trifluoromethyl group, a trifluoromethoxy group, an optionally protected hydroxyl group, an alkyl group optionally having substituents, a cycloalkyl group optionally having substituents, an aryl group optionally having substituents, an aralkyl group optionally having substituents, an alkoxyl group optionally having substituents or an aryloxy group optionally having substituents, which comprises:

reacting a quinolinecarbaldehyde of the formula (I)

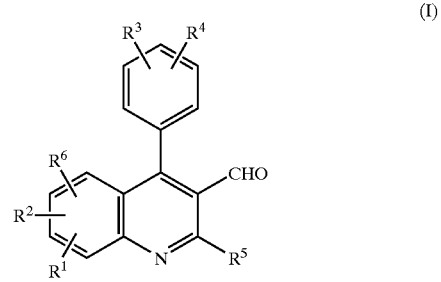

(I)

wherein $R^1$, $R^2$, $R^3$, $R^4$, $R^5$ and $R^6$ are as defined above, with any of the following compounds (a) to (c) in the presence of a base, (a) a phosphonium salt compound of the formula (II)

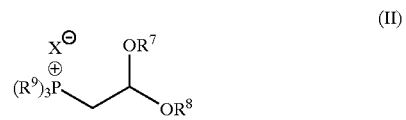

(II)

wherein $R^7$ and $R^8$ each independently represent a hydrogen atom, an alkyl group optionally having substituents, an acyl group optionally having substituents or an aralkyl group optionally having substituents, or in combination represent an alkylene group, an arylene group or an aralkylene group, $R^9$ represents an alkyl group optionally having substituents or an aryl group optionally having substituents, and X represents a halogen atom, (b) a phosphonate compound of the formula (III)

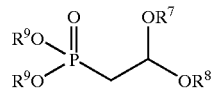

(III)

wherein $R^7$, $R^8$ and $R^9$ are as defined above, and
(c) a phosphonate compound of the formula (IV)

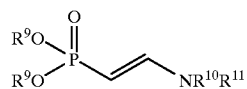

(IV)

wherein each $R^9$ is as defined above, and $R^{10}$ and $R^{11}$ each independently represent a hydrogen atom, an alkyl group optionally having substituents, a cycloalkyl group optionally having substituents, an aryl group optionally having substituents or an aralkyl group optionally having substituents, or in combination represent an alkylene group, an arylene group or an aralkylene group,
and then hydrolyzing the resulting compound.

2. The production method of a quinoline derivative of claim 1, wherein $R^1$, $R^2$, $R^3$ and $R^6$ are hydrogen atoms, $R^4$ is a halogen atom, $R^5$ is an alkyl group having 1 to 6 carbon atoms or a cycloalkyl group having 3 to 6 carbon atoms, $R^7$ and $R^8$ are each independently an alkyl group having 1 to 6 carbon atoms, a cycloalkyl group having 3 to 6 carbon atoms, a phenyl group, a naphthyl group or a benzyl group, or in combination show an alkylene group having 2 to 6 carbon atoms or an arylene group having 6 to 10 carbon atoms, $R^9$ is an alkyl group having 1 to 6 carbon atoms or a phenyl group, and $R^{10}$ and $R^{11}$ are each independently an alkyl group having 1 to 6 carbon atoms, a cycloalkyl group having 3 to 6 carbon atoms, a phenyl group, a naphthyl group or a benzyl group, or in combination show an alkylene group having 2 to 6 carbon atoms or an arylene group having 6 to 10 carbon atoms.

3. The production method of a quinoline derivative of claim 2, wherein $R^4$ is a fluorine atom, $R^7$ and $R^8$ are each independently an alkyl group having 1 to 6 carbon atoms, or in combination show an alkylene group having 2 to 6 carbon atoms, and $R^{10}$ and $R^{11}$ are each independently an alkyl group having 1 to 6 carbon atoms, or in combination show an alkylene group having 2 to 6 carbon atoms.

* * * * *